US006994683B1

(12) United States Patent
Starr

(10) Patent No.: US 6,994,683 B1
(45) Date of Patent: Feb. 7, 2006

(54) PORTABLE LUMBAR TRACTION DEVICE

(76) Inventor: David Starr, 4926 Jacques St., Torrance, CA (US) 90503

( * ) Notice: Subject to any disclaimer, the term of this patent is extended or adjusted under 35 U.S.C. 154(b) by 0 days.

(21) Appl. No.: 10/912,406

(22) Filed: Aug. 4, 2004

(51) Int. Cl.
*A61F 5/00* (2006.01)

(52) U.S. Cl. ............................ 602/32; 602/36; 602/33; 482/121; 482/129

(58) Field of Classification Search .................. 602/32, 602/33, 35, 36; 128/845, 875, 876; 482/92, 482/95, 114, 121, 122–124, 129–130, 131, 482/904, 907
See application file for complete search history.

(56) References Cited

U.S. PATENT DOCUMENTS 2,701,564 A * 2/1955 Wilhelm ...................... 602/32
2,954,026 A 9/1960 Spinks
3,105,489 A * 10/1963 Zivi ............................ 602/32
4,483,330 A 11/1984 Jacobsen et al.
4,641,637 A * 2/1987 Rosen ......................... 602/35
4,865,022 A 9/1989 Gorsen
4,869,240 A 9/1989 Boren
4,971,043 A * 11/1990 Jones .......................... 602/36
5,092,322 A * 3/1992 Gantz .......................... 602/35
5,328,433 A 7/1994 Berman
5,368,281 A * 11/1994 Skyba ........................ 254/391
5,387,186 A * 2/1995 Edland ........................ 602/36
5,672,157 A * 9/1997 Gallagher et al. ............ 602/32
5,848,984 A * 12/1998 Bachar et al. ................ 602/32
6,045,525 A * 4/2000 Chitwood .................... 602/36
6,113,564 A * 9/2000 McGuire ..................... 602/32
6,190,345 B1 2/2001 Henderson
6,258,050 B1 7/2001 Henderson
6,648,844 B2 11/2003 Kamerman
6,708,693 B1 * 3/2004 Choy et al. ................. 128/845
2003/0018287 A1 1/2003 Gilliam

* cited by examiner

*Primary Examiner*—Henry Bennett
*Assistant Examiner*—Amanda Wieker
(74) *Attorney, Agent, or Firm*—Fulwider Patton, LLP

(57) ABSTRACT

A portable lumbar traction device wherein a variable tension system allows the user to manually manipulate a level of tension using a ratcheting device while undergoing a traction procedure. The invention easily and quickly anchors to a door frame and includes one or more springs to create tension in the device. A belt or harness worn by the user couples to a cable or tether in tension with the spring, and the ratcheting device incrementally increases the tension when actuated by the user until the desired tension level is achieved.

4 Claims, 3 Drawing Sheets

PORTABLE LUMBAR TRACTION DEVICE

FIELD OF THE INVENTION

The present invention relates generally to apparatus used to treat lower back pain, and more particularly to a portable lumbar traction device used for applying therapeutic tension of varying magnitudes to a patient.

BACKGROUND OF THE INVENTION

Back pain is the most frequent and expensive health care problem in adults between the ages of 30–50, and is the most common cause of work loss and disability. Eighty-five percent of the people will suffer some form of back discomfort ranging from intermittent back pain to disability at some time during their lives. For all ages, back pain is the most common cause of activity avoidance (such as golf, gardening, hiking, etc.). Noted back specialists concur that back pain is a symptom of physical dysfunction—i.e., the back is not moving and working as it should. Recovery and relief of pain depends on getting one's back moving and working again and restoring normal function. Medical science has proven that sitting compresses the spine more than any activity and is a major cause of spinal dysfunction. Americans are sitting more and more each year, which is a major reason why back pain has become an epidemic and is currently the most expensive medical diagnosis in America—over $100 billion a year. Lumbar traction helps to decompress the spine and restore function. When applied by the patient at home, it drastically reduces the cost to the patient, insurance companies, and society.

The typical tension necessary for lumbar traction may eventually require a tension force up to approximately one half to two thirds of a patient's weight, depending upon the patient's tolerance, the severity of the injury, and the stage of recovery/rehabilitation. Forces of this magnitude can require special equipment that is usually limited to doctors and chiropractor's offices. This can be both inconvenient and expensive for the patient, and unnecessarily crowd therapist's offices while patients undergo lumbar or other tractions. Currently, the fear of being stranded with back pain keeps countless back pain sufferers restricted in their ability to travel and participate in outdoor activities. Moreover, the traveler, camper, hiker, golfer, etc. who is in need of relief and away from his practitioner may have to forego treatment due to a lack of available equipment.

Attempts to create a sufficiently low cost portable traction device for home use have thus far produced unsatisfactory results. Today, many portable traction devices operate on inversion therapy. However, the traction created by hanging upside down has numerous disadvantages. For one, they create considerable intracranial pressure that can lead to several ill effects such as headaches and ocular dysfunction. Second, when in acute pain these devices are very difficult to get in and out of, often causing additional pain or leading to further injury. Third, they commonly rely on an "all or nothing" force, where the patient is fully suspended or not suspended at all with no intermediate position. Fourth, the maximum force is limited by one's body weight. Fifth, the are very bulky and heavy, making them extremely difficult to travel with. Consequently, in the beginning of treatment the force is often too much, and then insufficient in the latter stages of therapy. Other less common traction units include a simple mechanical pulley systems that require the patient to physically apply the required tension while undergoing the treatment. This can be tiring for the patient, and uneven or misapplied tension can result that can further injure the patient. Other portable traction devices utilize pneumatic or hydraulic cylinders to create the traction force. Hydraulic cylinders have the disadvantage of the weight of the hydraulic fluid, making travel with such devices impractical. Pneumatic cylinders with low pressure inputs typically can not maintain an adequate traction force for a sufficient period of time to be effective in a traction device. Thus, the art is in need of a portable lumbar traction device that is easily mounted and stored, while providing variable tensions that suit changing patient needs.

SUMMARY OF THE INVENTION

The present invention is directed to a portable traction device that includes a coiled spring for providing tension to a harness or waist belt worn by the user, and a ratchet operable by the user to adjust the tension applied by the spring. The ratchet may be actuated by a pole or tether controlled by the user to increase or decrease the tension in the lumbar traction device. The spring is further connectable to a door or door frame, post, tree, car bumper, or suitable rigid structure, so that the device is particularly suited for travel or home use. For example, the spring may be connected via a tether to a pipe, block, or the like that is placed on the outside of a closed door with the tether passing underneath the door such that the pipe, block, etc. serves as an anchor. The ratchet can be used to expand the spring's tension and thus apply varying pressure to the patient's spine through the harness or vest. A pole or the like is linked to the ratchet to enable the user, while prone, to sequence the ratchet to gradually higher tensions until the appropriate, comfortable tension is achieved. The invention may use interchangeable springs or heavy rubber tie downs of different tension capabilities to allow even greater flexibility in the available degree of traction. In a first embodiment of the invention, the traction apparatus folds up into a carrying case that is approximately 14"×16"×2" and weighs less that seven pounds, serving as an effective portable traction device that can be used at home, work, in hotels, camping, hiking, and the like.

DETAILED DESCRIPTION OF THE INVENTION

The present invention is a tensioning device that is portable and capable of mounting or connecting to a common door frame or fixed structure that selectively applies lumbar traction to a patient. The device of the present invention includes an anchoring section that can be used to secure the device to a door frame or the like, a tension producing section that includes a mechanical spring coupled to a ratchet mechanism for increasing the spring's tension, and a belt or harness section that is worn by the user. The belt or harness can be used in conjunction with a pad or mat that incorporates a frictional surface that resists sliding of the pad or mat on the supporting surface such as a carpet, grass, or floor. Each of the three sections will be discussed in turn.

Figure 1:
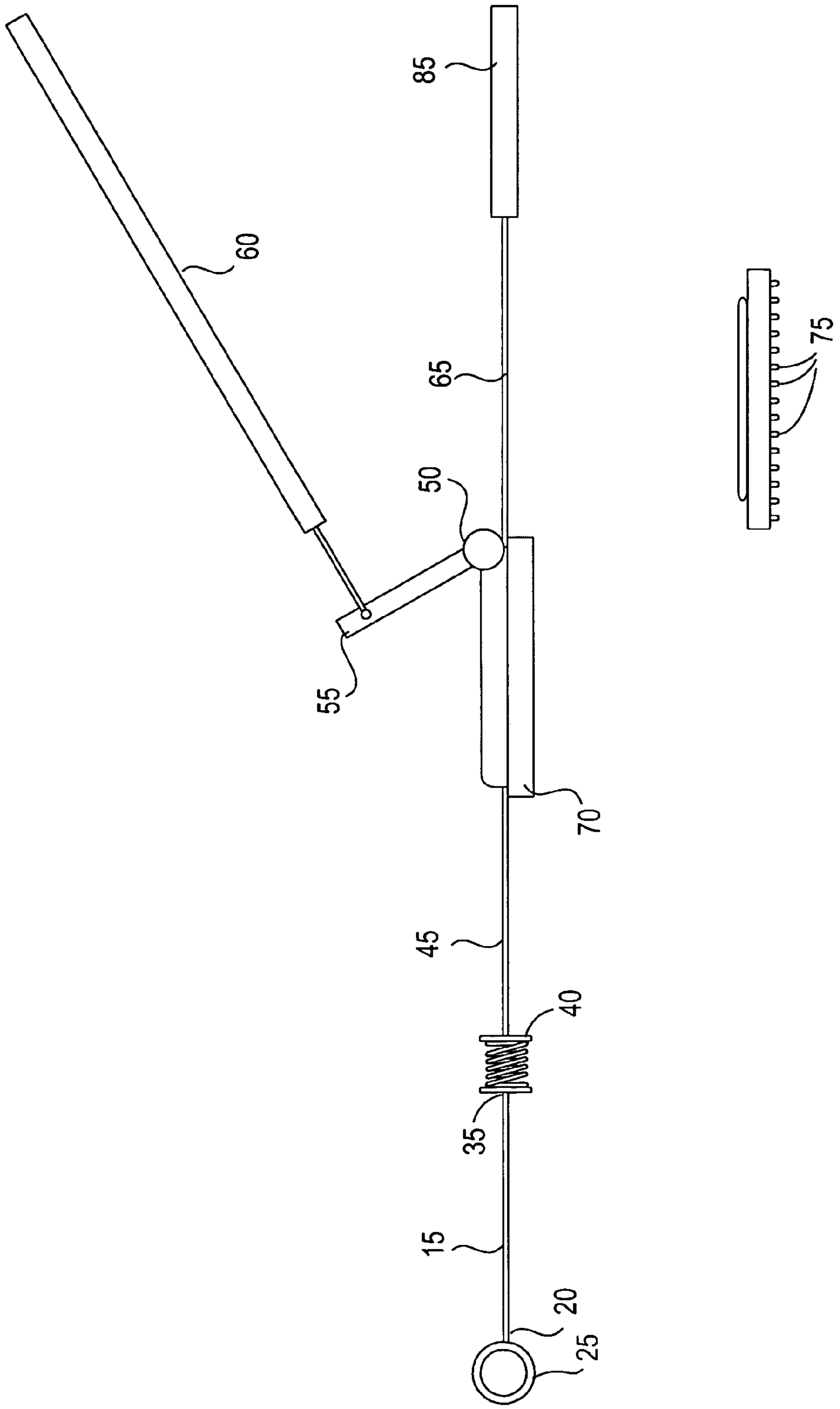
FIG. 1 is a schematic side view of a first embodiment of the present invention.
Figure 2:
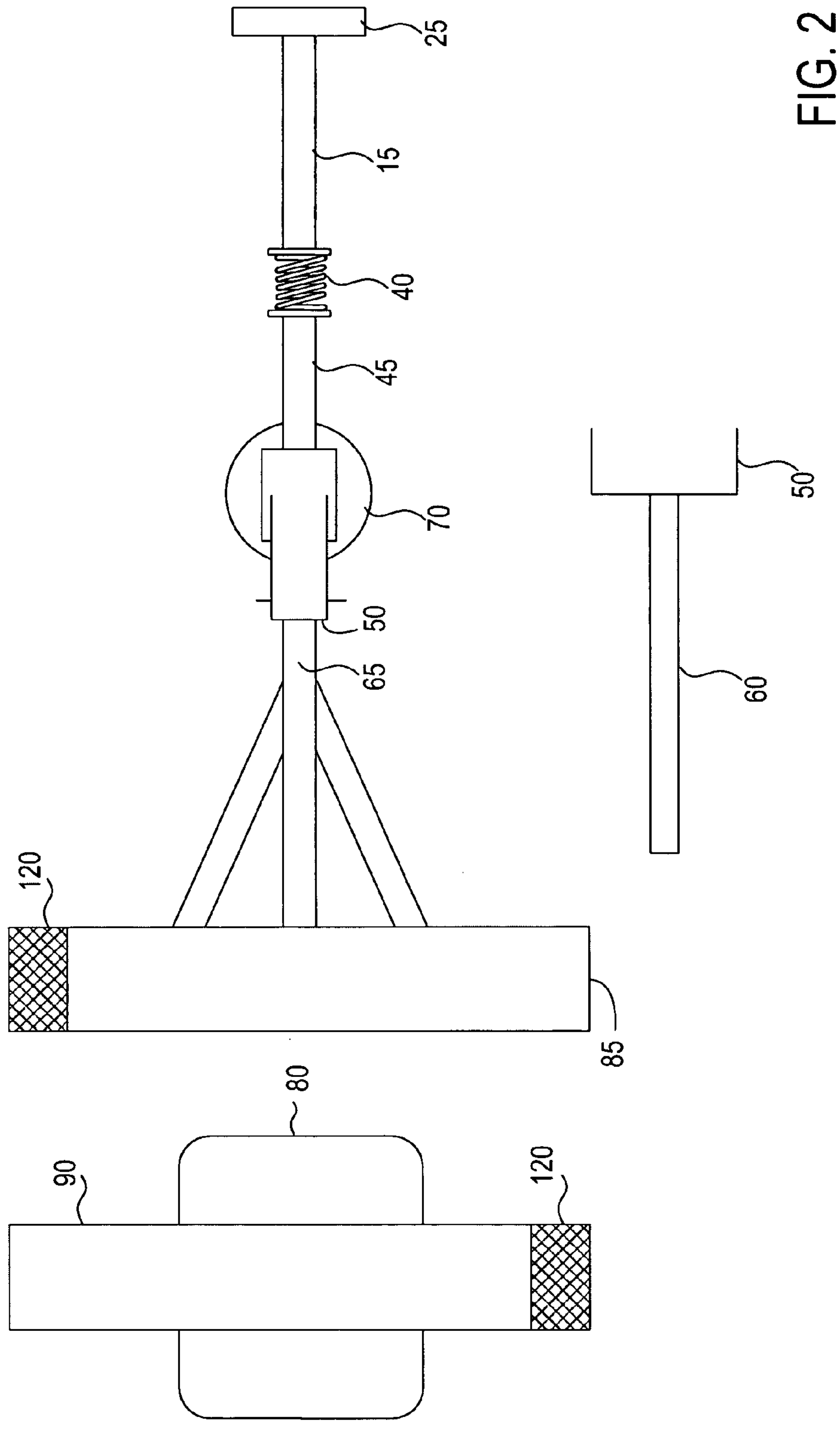
FIG. 2 is a schematic top view of the embodiment of FIG. 1.

The anchoring section of the lumbar device in a first embodiment is a non-resilient nylon tether 15 or belt connected at a distal end 20 to a plastic pipe 25 as shown in FIGS. 1 and 2. The pipe 25 is placed behind a door 30 with the nylon tether 15 passing underneath the door 30 such that tension applied to the nylon tether will be transferred by to the pipe 25 to the outside of the door. As long as tension applied to the tether 15 at the proximal end 35 does not exceed the deformation limit of the nylon tether or the connection measures at the pipe 25, the tether 15 will remain in tension. While a pipe is shown, the anchoring component can be any number of shapes and requires only that it be substantially thicker that the gap between the door and the floor so that it abuts up against the outside of the door when tension is applied to the proximal end of the nylon tether. Alternatively, the anchoring mechanism can be an expandable bar (not shown) that fits across the door frame and expands therein (typically using a threaded member) so was to wedge into the door frame. The expandable bar is collapsible only when deactivated by the user to prevent unexpected loss of tension that can injure a patient. Other forms of anchoring to a door frame may include a hook adapted to releasably lock on to a door frame or door itself, and a clamp that rigidly secures to a door frame until removed by the patient.

The tensioning section of the device comprises a coiled mechanical spring 40 coupled to the proximal end 35 of the nylon tether 15. When the spring 40 is expanded, it applies a predictable and repeatable force that varies proportional to the distance displaced under a formula known as Hooke's law. That is, in a spring where x is the displacement of spring from equilibrium, then the expression $$F=-kx$$

holds where k is the spring constant (force per unit of distance) as long as the elastic limit of the spring is not exceeded. Thus, for a constant displacement of the spring a constant force or tension will result. This predictability is beneficial when a patient seeks to repeat a traction procedure in that a known displacement will repeatably produce a known traction. Further, a supervising physician or practitioner can establish limits during an office visit and be confident that if the patient follows the proper instructions then the proper amount of tension will be applied in his or her absence.

The spring 40 is coupled via a second nylon tether 45 to a ratcheting device 50 that can incrementally displace the spring 40 using a lever 55 or the like to gradually increase the tension of the device. The ratchet mechanism 50 can be supported on a base 70 or platform constructed of a heavier material such as wood or rubber. The ratchet 50 may be of a belt type that advances a belt as the lever 55 is pivoted, where the advancement of the belt is coupled to the nylon tether 45 to "pull" it against the force of the spring 40. Each movement of the ratchet displaces the spring by predetermined distance, and according to Hooke's law each advancement increases the tension in the spring by an equal measure. Other types of ratchets include those with a toothed wheel that is driven one tooth at a time by a complimentary component called a pawl. Rotation is achieved by bearing the pawl against the toothed wheel causing the toothed wheel to advance one tooth at a time. The distance between each tooth on the arc of the wheel represents an increment of displacement of the mechanical spring as the wheel is rotated. Ratchets can be either single direction or dual direction devices, and the present invention contemplates the use of either type of ratchet but single direction ratchets provide the benefit of simpler operation.

Advancing the ratchet 50 incrementally to increase the tension in the device is preferably accomplished using a manual implement such as a pole 60, rope, or cable. The pole 60 connects to the lever 55 (or pawl alternate ratchet actuator) and is used by the patient to operate the lever 55. For example, as shown in FIGS. 1 and 2, a pole 60 coupled to the ratchet lever 55 can be used by the patient to advance the ratchet 50 as required while the patient is prone and engaged with the device. The patient pushes the pole 60 to rotate/pivot the connected lever 55 which in turn advances the ratchet 50 and increases the tension applied to the patient. If the ratchet 50 is a one-way mechanism, each stroke of the pole 60 advances the ratchet a single displacement of the spring 40 and thereby increases the tension in the device by a predictable and repeatable value. The ratchet 50 can be advanced with other implements such as a chain or rope, foot pedal, or any number of means for translating displacement.

The third element of the invention is the belt or harness section that is worn by the patient to apply the tension created by the spring 40 and ratchet 50 to the patient. The belt or harness is connected to the ratchet 50 by another non-resilient tether 65 or other flexible, non-stretching component that will translate the tension in the device to the patient. The belt or harness preferably releasably attaches to the tether 65 using a clip or other fastener (not shown) that allows the user to first adorn the belt or harness and then attach the tether to begin the procedure.

Because the tension is applied parallel to the surface of the floor, it may be necessary to ensure that the patient does not slide in the direction of the tension, which negates the beneficial application of the force. That is, in order to apply tension to the patient, the patient must remain stationary in the presence of a horizontal force tending to move the patient against the frictional forces between the patient and the floor. To enhance the frictional forces and therefore resist slippage, the belt or harness may comprise small spikes or rubber nubs 75 located at the external dorsal regions so as to engage the carpet or floor when the patient is prone on his or her back. Other means of increasing the frictional forces include ridges on the belt or other non-smooth surfaces positioned for engagement with the floor.

Alternatively, the belt or harness may be coupled with a mat or pad 80 that is laid on the floor and may be heavy enough to resist slipping. The pad or mat 80 will have a larger surface area than the contact between the patient's back and the floor affording a larger frictional surface to resist sliding. The engagement of the belt or harness and the pad or mat can be achieved using a hook and loop fastener such as VELCRO® fastener to resist slippage between the mat or pad 80 and the belt or harness. The pad or mat can further be equipped with small spikes or projections (not shown) that engage the carpet and prevent the pad or mat from sliding along the floor. Also, the harness can be two separate components as shown in FIG. 2, a waist belt 85 and a separate chest belt 90. The waist belt 85 is connected to the ratchet 50 at the nylon tether 65 to apply traction to the patient's lumbar region, and the chest belt 90 is used to anchor the patient to the complimentary mat or pad 80 using the hook and loop fastener material or alternative securing means.

In a preferred embodiment, the device includes a display 95 that can inform the patient of the current force or tension in the device. The display 95 is coupled to a processor that has a stored program for each spring used, converting the displacement of the spring to a force using Hooke's law. The displacement can be measured in various ways, such as using strain gauges 100 on the nylon tether 15 to measure the strain in the tether. Using another well known formula, the strain can readily be converted to the stress in the tether which is a function of the force applied. The strain gauge 100 sends a signal to the processor using a cable or wire 105, and the processor calculates the present force or tension and communicates the tension to the display. The display 95 can be hung on a door knob 110 or connected to the door frame so as to be in view of the patient during the procedure. The display 95 can be an LED or liquid crystal display that can be viewed from various angles. In a preferred embodiment the display can include a strap 115 or hook that could allow the display 95 to suspend from the door knob, or a clip that can secure to the edge of a door.

Figure 3:
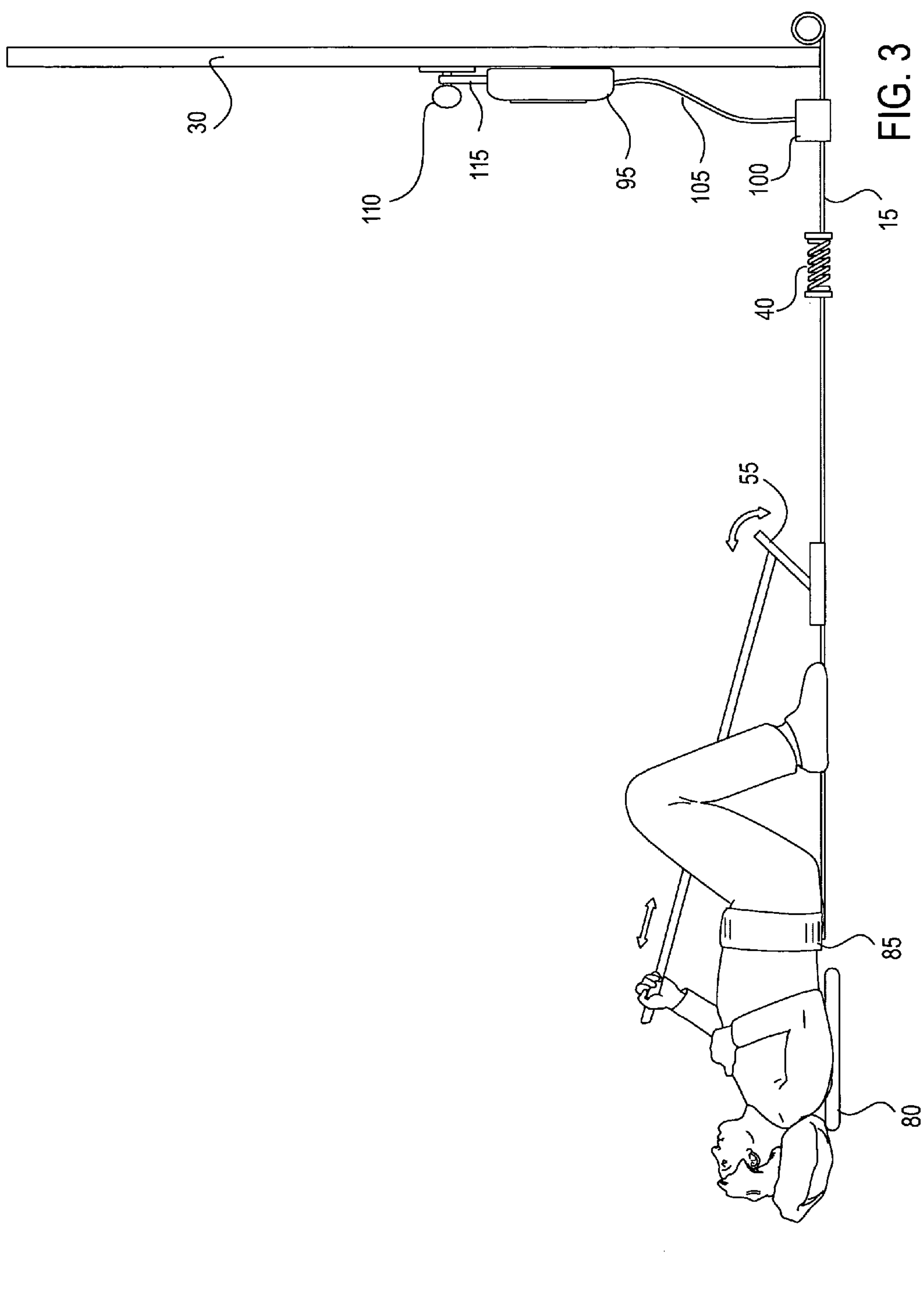
FIG. 3 is a diagram of a user operating the embodiment of FIG. 1.

In operation (see FIG. 3), the patient will typically adorn the waist belt 85 and chest belt 90 initially using a hook and loop patch 120, or straps with buckles or hook and loop fastening material to secure the chest and waist belts. A single piece harness can also substitute for the two belts. A mat or pad 80 with friction enhancing lower surface is placed on the floor approximately five to ten feet from a door frame. The patient takes the anchoring mechanism and locks the device to the door frame. This can be the pipe 25 shown in FIG. 1 placed either between the door and the door frame or behind the closed door 30 with the attached tether 15 passing around the door 30 thereby fixing the pipe 25 against the outside surface of the door 30. Next the ratchet device 50 mounted on its base 70 is placed on the floor away from the door such that the nylon belts 15,45 are taught and there is slight tension in the spring 40. The lever 55 or actuator of the ratchet 50 is connected to a pole 60, cable, rope, or other elongate member that can be grasped by the patient when prone. If the device includes a display 95, the display is mounted or set up in a location that will be visible to the patient from the prone position. The display 95 is turned on to reveal the tension in the device.

Sitting on the mat or pad 80, the patient connects the tether 65 to the waist belt 85 or harness using a clasp or hook mechanism so that a continuous connection is made between the anchoring section, the spring 40 and adjacent nylon tethers, the ratchet mechanism 50 and adjacent tethers, and the patient's waist belt 85. Tension developed by the spring 40 is transferred to the anchoring mechanism at the door frame and the patient through traction. The patient then reclines with the chest belt 90 on the mat 80 such that hook and loop fastener material on the pad or mat and chest belt cooperate to resist slipping across the mat or pad. Using the pole 60, the patient pulls the lever arm 55 of the ratchet 50 to advance the ratchet 50 in a predetermined direction. Each advance of the ratchet 50 displaces the proximal end of the spring 40 by a known distance, which in turn increases the spring's resistive force by a substantially equal amount. The resistive force of the spring 40 is converted to tension on the patient because the anchoring member of the device is fixed to the door 30 or the door frame. The patient continues to advance the ratchet 50 and increase the tension in the device until a satisfactory level is reached. The tension is maintained while the patient undergoes the therapeutic benefits of the traction applied to the lumbar region.

It is to be understood that the foregoing description is merely illustrative and those embodiments described should not be used to limit the scope of the invention in any way. No attempt has been made to restrict or limit the invention to the disclosed embodiments, and the scope of the invention should be determined from the claims appended hereto.

I claim:

1. A portable lumbar traction device adapted to work on a floor and with a door and door fame comprising:

a tubular anchor having a diameter larger than a distance between said door and said floor when said door is closed;

a tether having first and second ends, said first end connected to said tubular anchor, said tether adapted to pass under said closed door and having a length such that said second end is spaced from said closed door;

a spring having first and second ends, said first end of said spring connected to said second end of said tether;

a belt worn by a patient having straps for applying a traction to said patient when said straps are placed in tension; and a tension advancing mechanism comprising:

a weighted platform having an upper and lower planar surfaces, said lower planar surface in contact with said floor during operation of said portable lumbar traction device and said upper planar surface supporting a ratchet thereon, said weighted platform disposed directly between said spring and said belt;

a ratchet pivotally mounted to said weighted platform on said upper surface and engaging a distal end of straps of said belt for incrementally advancing said straps;

an actuator lever having first and second ends and extending radially outward from said pivotally mounted ratchet, said actuator lever connected to said ratchet at said first end and said second end including an aperture for engaging a pole; and a pole adapted to engage said second end of said actuator lever at said aperture to rotate said ratchet and reduce a length of strap between said belt and said ratchet.

2. The portable lumbar traction device of claim 1 further comprising a display for showing a tension developed in the device.

3. The portable lumbar traction device of claim 1 further comprising a strain gauge.

4. The portable lumbar traction device of claim 1 further comprising a chest belt cooperating with a mat to resist slippage between a user and the floor.

* * * * *